US00PP22877P2

(12) United States Plant Patent
Geibel

(10) Patent No.: US PP22,877 P2
(45) Date of Patent: Jul. 24, 2012

(54) GERANIUM PLANT NAMED 'PACYELLIM'

(50) Latin Name: *Pelargonium×hortorum*
Varietal Denomination: Pacyellim

(75) Inventor: Martin Geibel, Dresden (DE)

(73) Assignee: Elsner PAC Jungpflanzen, Dresden (DE)

( * ) Notice: Subject to any disclaimer, the term of this patent is extended or adjusted under 35 U.S.C. 154(b) by 0 days.

(21) Appl. No.: 13/064,707

(22) Filed: Apr. 9, 2011

(51) Int. Cl.
*A01H 5/00* (2006.01)

(52) U.S. Cl. ..... Plt./325

(58) Field of Classification Search ..... Plt./325
See application file for complete search history.

*Primary Examiner* — Kent L Bell

(74) *Attorney, Agent, or Firm* — C. A. Whealy

(57) ABSTRACT

A new and distinct cultivar of Zonal Geranium plant named 'Pacyellim', characterized by its compact, upright and uniformly rounded plant habit; freely branching habit; moderately vigorous growth habit; dark green-colored leaves; early and freely flowering habit; and semi-double yellow-colored flowers.

1 Drawing Sheet

Botanical designation: *Pelargonium×hortorum*.
Cultivar denomination: 'PACYELLIM'.

BACKGROUND OF THE INVENTION

The present invention relates to a new and distinct cultivar of Zonal Geranium plant, botanically known as *Pelargonium×hortorum*, and hereinafter referred to by the name 'Pacyellim'.

The new Zonal Geranium plant is a product of a planned breeding program conducted by the Inventor in Dresden, Germany. The objective of the breeding program is to create new uniform Zonal Geranium plants with attractive leaf and flower coloration.

The new Zonal Geranium plant originated from a cross-pollination made by the Inventor in Dresden, Germany during the summer of 2006 of two unnamed proprietary selections of *Pelargonium×hortorum*, not patented. The new Zonal Geranium plant was discovered and selected by the Inventor as a flowering plant from within the progeny of the stated cross-pollination in a controlled environment in Dresden, Germany during the spring of 2007.

Asexual reproduction of the new Zonal Geranium plant by vegetative terminal cuttings in a controlled environment in Dresden, Germany since January, 2008, has shown that the unique features of this new Zonal Geranium plant are stable and reproduced true to type in successive generations.

SUMMARY OF THE INVENTION

Plants of the new Zonal Geranium have not been observed under all possible environmental conditions and cultural practices. The phenotype may vary somewhat with variations in environment such as temperature and light intensity without, however, any variance in genotype.

The following traits have been repeatedly observed and are determined to be the unique characteristics of 'Pacyellim'. These characteristics in combination distinguish 'Pacyellim' as a new and distinct Zonal Geranium plant:

1. Compact, upright and uniformly rounded plant habit.
2. Freely branching habit.

3. Moderately vigorous growth habit.
4. Dark green-colored leaves.
5. Early and freely flowering habit.
6. Semi-double yellow-colored flowers.

Plants of the new Zonal Geranium differ primarily from plants of the parent selections in plant vigor and flower color.

Plants of the new Zonal Geranium can be compared to plants of the *Pelargonium×hortorum* 'Pacyell', disclosed in U.S. Plant Pat. No. 20,906. In side-by-side comparisons conducted in Dresden, Germany, plants of the new Zonal Geranium differed from plants of 'Pacyell' in the following characteristics:

1. Plants of the new Zonal Geranium were more vigorous than plants of 'Pacyell'.
2. Plants of the new Zonal Geranium were more freely branching than plants of 'Pacyell'.
3. Plants of the new Zonal Geranium had slightly darker yellow-colored flowers than plants of 'Pacyell'.
4. Plants of the new Zonal Geranium had shorter peduncles and pedicels than plants of 'Pacyell'.

BRIEF DESCRIPTION OF THE PHOTOGRAPH

The accompanying colored photograph illustrates the overall appearance of the new Zonal Geranium plant showing the colors as true as it is reasonably possible to obtain in colored reproductions of this type. Colors in the photograph may differ slightly from the color values cited in the detailed botanical description which accurately describe the colors of the new Zonal Geranium plant.

The photograph comprises a side perspective view of a typical flowering plant of 'Pacyellim' grown in a container.

DETAILED BOTANICAL DESCRIPTION

The aforementioned photograph and following observations, measurements and values describe plants grown during the winter and spring in 13-cm containers in a glass-covered greenhouse in Dresden, Germany and under conditions which closely approximate commercial Zonal Geranium production. During the production of the plants, day temperatures averaged 18° C., night temperatures averaged 16° C. and light levels ranged from 15 kilolux to 100 kilolux. Plants were three months old when the photograph was taken, and plants were six months old when the description was taken. In the detailed description, color references are made to The Royal Horticultural Society Colour Chart, 1995 Edition, except where general terms of ordinary dictionary significance are used.

Botanical classification: *Pelargonium×hortorum* 'Pacyellim'.

Parentage:

*Female, or seed, parent*.—Unnamed proprietary selection of *Pelargonium×hortorum*, not patented.

*Male or pollen parent*.—Unnamed proprietary selection of *Pelargonium×hortorum*, not patented.

Propagation:

*Type*.—By vegetative terminal cuttings.

*Time to initiate roots, summer*.—About 18 days at temperatures of 20° C.

*Time to initiate roots, winter*.—About 22 days at temperatures of 20° C.

*Time to produce a rooted young plant, summer*.—About 30 days at temperatures of 20° C.

*Time to produce a rooted young plant, winter*.—About 30 days at temperatures of 18° C.

*Root description*.—Fine, fibrous; white in color.

*Rooting habit*.—Freely branching; dense.

Plant description:

*Plant/growth habit*.—Compact, upright and uniformly rounded plant habit; densely foliated; moderately vigorous growth habit; freely basal branching habit with about 20 lateral branches developing per plant.

*Plant height, to top of umbels*.—About 30 cm.

*Plant height, to top of leaves*.—About 20 cm.

*Plant width*.—About 30 cm.

*Lateral branches*.—Length: About 7 cm. Diameter: About 5 mm. Internode length: About 5 mm to 10 mm. Texture: Pubescent. Color: Close to 144A.

Foliage description:

*Arrangement*.—Alternate and opposite; simple.

*Length*.—About 3 cm to 5 cm.

*Width*.—About 5 cm to 7 cm.

*Shape*.—Cordate, rounded.

*Apex*.—Rounded.

*Base*.—Cordate.

*Margin*.—Crenate.

*Venation pattern*.—Palmate.

*Texture, upper and lower surfaces*.—Pubescent; leathery.

*Color*.—Developing and fully expanded leaves, upper surface: Close to 147A; venation, close to 146C. Developing and fully expanded leaves, lower surface: Close to 147B; venation, close to 146C.

*Zonation pattern*.—Not discernible.

*Petiole*.—Length: About 3 cm to 7 cm. Diameter: About 2 mm. Texture, upper and lower surfaces: Pubescent. Color, upper and lower surfaces: Close to 144A.

Flower description:

*Flower arrangement*.—Single semi-double flowers arranged in rounded hemispherical umbels arising from apical leaf axils; umbels displayed above the foliar plane on strong peduncles; flowers mostly flat and face upright to outward depending on the position in the umbel.

*Fragrance*.—None detected.

*Quantity of flowers*.—Freely flowering habit; about 15 umbels develop per plant; each umbel with about nine flower buds and open flowers.

*Flowering season*.—Early flowering habit, plants begin flowering about 65 days after planting; in the greenhouse, plants flower year-round; in the garden in Germany, flowering is continuous from April until frost in the autumn.

*Flower longevity*.—Individual flowers last about six to ten days on the plant; umbels last about three to four weeks on the plant; flowers not persistent.

*Umbel height*.—About 4 cm.

*Umbel diameter*.—About 6.5 cm.

*Flower diameter*.—About 3.5 cm.

*Flower depth* (*height*).—About 1 cm.

*Flower buds*.—Length: About 7 mm. Diameter: About 4 mm. Shape: Roughly elliptic. Color: Close to 144A.

*Petals*.—Quantity and arrangement: Nine per flower arranged in a single whorl; petals imbricate. Length, upper and lower petals: About 1.5 cm to 2 cm. Width, upper and lower petals: About 6 mm to 14 mm. Shape: Roughly obovate. Apex: Rounded. Base: Attenuate. Margin: Entire. Texture, upper and lower surfaces: Smooth, glabrous. Color: When opening and fully opened, upper surface: Close to 1C; towards the base, close to 155A; venation, close to 1C; color becoming closer to 1D with development. When opening, lower surface: Close to 1C; towards the base, close to 155D; venation, close to 1C. Fully opened, lower surface: Close to 1D; towards the base, close to 155D; venation, close to 1D.

*Petaloids*.—Quantity: One to five. Length: About 5 mm to 10 mm. Width: About 2 mm to 5 mm. Shape: Irregular. Apex: Rounded. Base: Attenuate. Margin: Entire. Texture, upper and lower surfaces: Smooth, glabrous. Color: When opening and fully opened, upper surface: Close to 1C; towards the base, close to 155A; venation, close to 1C; color becoming closer to 1D with development. When opening, lower surface: Close to 1C; towards the base, close to 155D; venation, close to 1C. Fully opened, lower surface: Close to 1D; towards the base, close to 155D; venation, close to 1D.

*Sepals*.—Quantity and arrangement: Five per flower arranged in a single whorl. Length: About 7 mm. Width: About 3 mm. Shape: Lanceolate. Apex: Acute. Margin: Entire. Texture, upper surface: Smooth, glabrous. Texture, lower surface: Pubescent. Color, upper and lower surfaces: Close to 144A.

*Peduncle* (*umbel stem*).—Length: About 10 cm to 15 cm. Diameter: About 2 mm. Strength: Strong. Angle: Mostly erect or outwardly slanted. Texture: Pubescent. Color: Close to 144A.

*Pedicel* (*individual flower stem*).—Length: About 1.5 cm to 2.5 cm. Diameter: About 1 mm. Strength: Strong; flexible. Texture: Pubescent. Color: Close to 144A.

*Reproductive organs*.—Androecium: Quantity of stamens: About eight per flower. Anther length: About 2 mm. Anther shape: Tubular. Anther color: Close to 172A. Pollen amount: Moderate. Pollen color: Close to 169A. Gynoecium: Quantity of pistils: One per flower. Pistil length: About 6 mm. Stigma shape: Five-parted. Stigma color: Close to 38B. Style length: About 1 mm. Style color: Close to 38D. Ovary color:

Close to 148C. Seeds: Seed development has not been observed on plants of the new Zonal Geranium.

Disease/pest resistance: Plants of the new Zonal Geranium have not been observed to be resistant to pathogens and pests common to Zonal Geraniums.

Garden performance: Plants of the new Zonal Geranium have been observed to tolerate rain, wind and temperatures ranging from about 1° C. to about 35° C. to 40° C. and have demonstrated good garden performance.

It is claimed:

1. A new and distinct Zonal Geranium plant named 'Pacyellim' as illustrated and described.

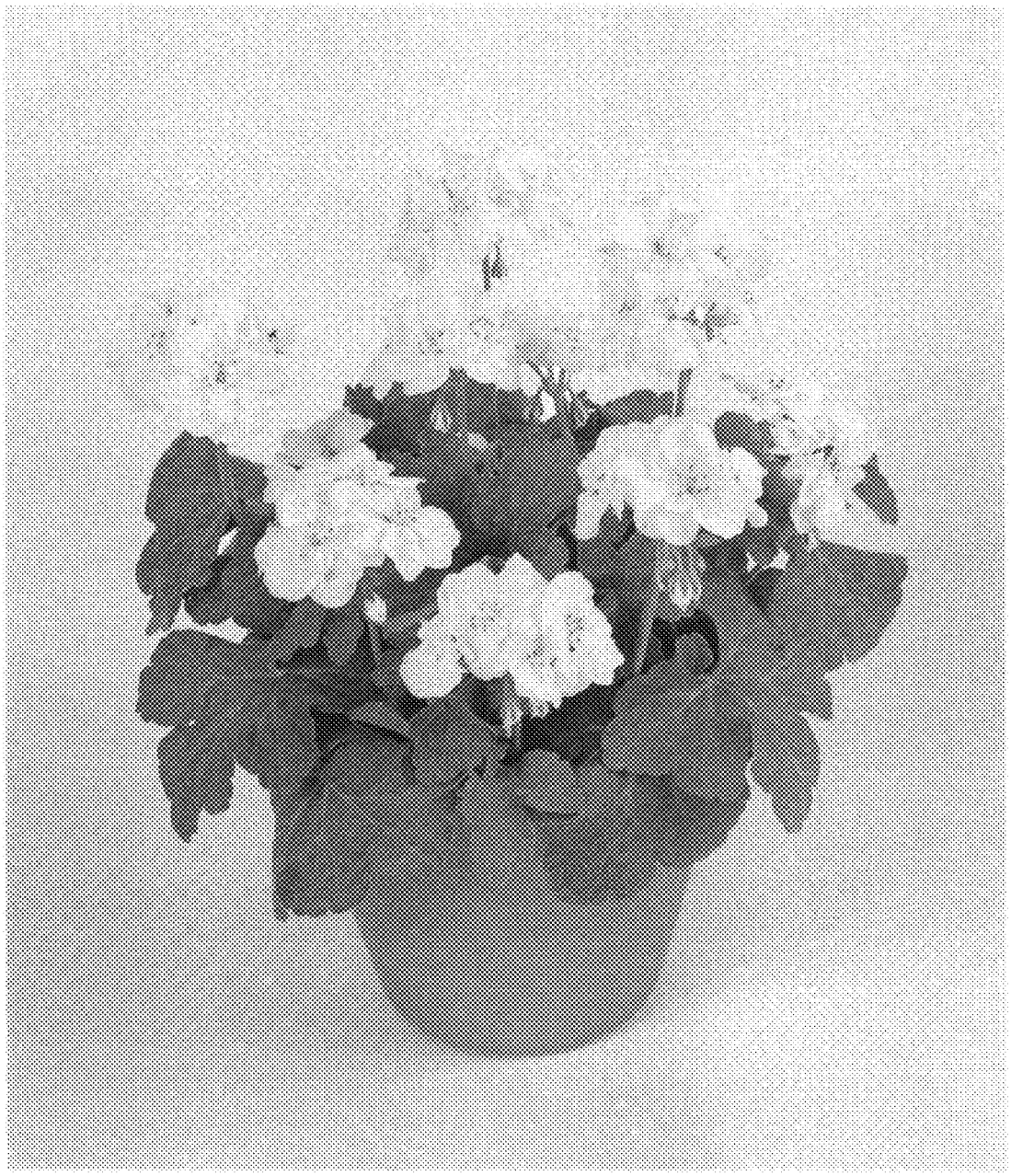

* * * * *